United States Patent [19]

Ueda et al.

[11] Patent Number: 4,532,363
[45] Date of Patent: Jul. 30, 1985

[54] PHENYLBUTYRALDEHYDES

[75] Inventors: Akiyoshi Ueda, Hiratsuka; Humiko Nagasaki, Oisomachi; Yutaka Takakura; Shigeru Kojima, both of Odawara, all of Japan

[73] Assignee: Nippon Soda Company Limited, Tokyo, Japan

[21] Appl. No.: 615,328

[22] Filed: May 30, 1984

Related U.S. Application Data

[62] Division of Ser. No. 485,910, Apr. 18, 1983, Pat. No. 4,471,126.

[30] Foreign Application Priority Data

Apr. 26, 1982 [JP] Japan ................................ 57-69847
Apr. 26, 1982 [JP] Japan ................................ 57-69848

[51] Int. Cl.³ .......................................... C07C 47/228
[52] U.S. Cl. ..................................... 568/424; 568/425
[58] Field of Search ..................... 568/424, 436, 425

[56] References Cited

U.S. PATENT DOCUMENTS 4,145,362 3/1979 Brepoels et al. ............... 260/465 G

OTHER PUBLICATIONS

Brepoels et al. (I), Chem. Abs., vol. 74 (1971) 42117b.
Poudreries Reunies Chem. Abs., vol. 74 (1971) 76154b.

Primary Examiner—Bernard Helfin
Attorney, Agent, or Firm—George B. Oujevolk

[57] ABSTRACT

There is a method for the production of 3-phenylpyrrole derivatives having the general formula

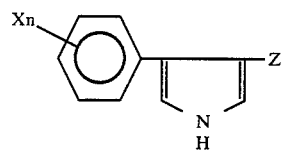

wherein
X is halogen, nitro or haloalkyl having 1 to 3 carbon atoms;
n is 0, 1 or 2; and
Z is hydrogen or halogen;
which comprises reacting a compound having the general formula

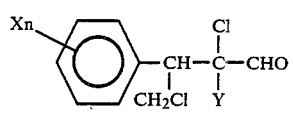

wherein
X and n are as previously defined; and
Y is hydrogen or halogen;
with ammonia or aqueous ammonia in an organic solvent.

A compound having the general formula [I] is useful as fungicide or intermediate thereof.

1 Claim, No Drawings

PHENYLBUTYRALDEHYDES

This is a divisional application of Ser. No. 06/485,910 filed Apr. 18, 1983 and now U.S. Pat. No. 4,471,126.

The present invention relates to a method for the production of 3-phenylpyrrole derivatives. Said 3-phenylpyrrole derivatives are useful as fungicides or intermediates thereof as described in U.S. Pat. No. 4,326,881 or U.S. Pat. No. 4,303,667.

Though methods for the production of said derivatives are already known as described below, their known methods have a large number of manufacturing steps and are complicated in operation so that they are barely desirable in commercial terms. Particularly, when chlorine substitution is effected at the 4-position, it needs that the both α-positions of pyrrole are protected by an easily leaving group before chlorination is performed at 4-position in view of the reactivity of pyrrole.

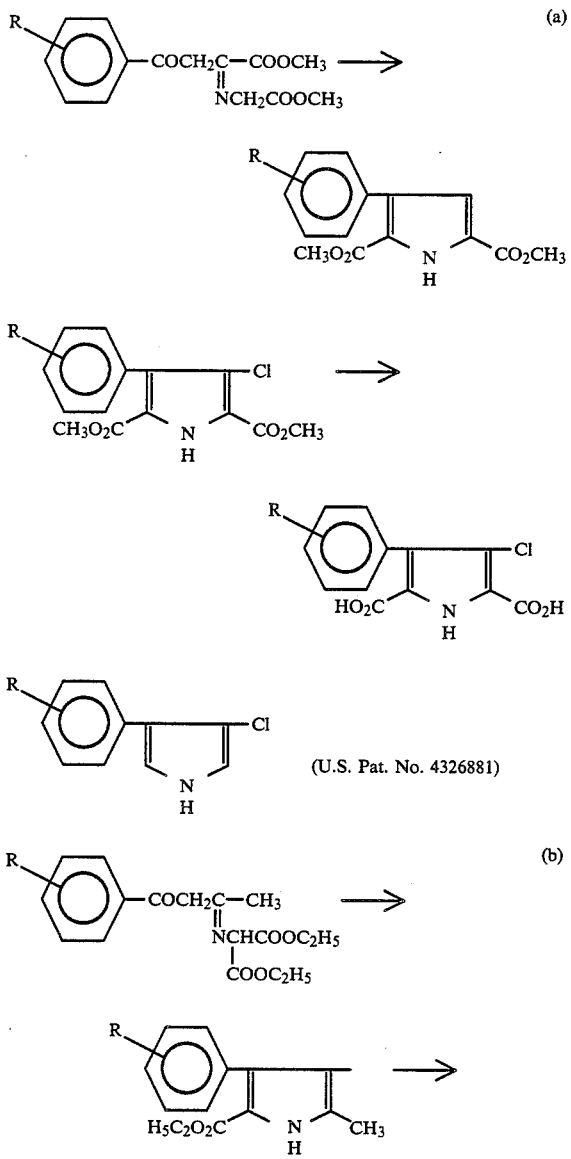

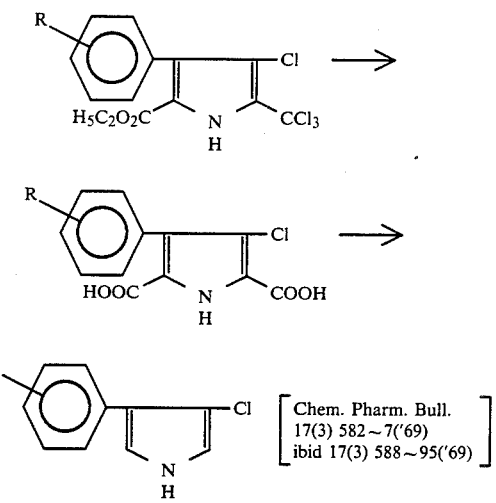

There is accordingly a need for a method for the production of 3-phenylpyrrole derivatives, which is able to employ for industrial menufacturing process by reason of providing a reduction of process under mild reaction conditions.

According to the present invention, there is provided a method for the production of 3-phenylpyrrole derivatives having the general formula

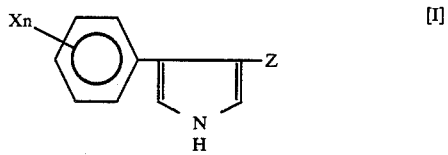

wherein
X is halogen, nitro or haloalkyl having 1 to 3 carbon atoms;
n is 0, 1 or 2; and
Z is hydrogen or halogen;
which comprises reacting a compound having the general formula

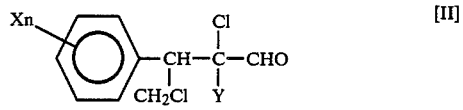

wherein
X and n are as previously defined; and
Y is hydrogen or halogen;
with ammonia or aqueous ammonia in an organic solvent. The reactions of cyclization and dehydrohalogenation are allowed to concur.

As an organic solvent, ethanol, methanol, dioxane, ethylene glycol dimethyl ether (glyme) and diethylene glycol dimethyl ether (diglyme) may be used.

The reaction temperature may be from 30° C. to the boiling point of the reaction solution, and the reaction may be carried out from 3 to 5 hours.

Furthermore, to improve the yield, the reaction solution can be cooled down to room temperature after the reaction and then the solution is kept at room temperature for several to 10 hours after a base is added to it.

As the base, triethylamine, sodium alkoxide, 1,8-diazabicyclo-[5,4,0]-7-undecene or the like may be used.

After the reaction has been completed, crude products are obtained in two ways. One is the use of ammonia gas as a reactant, where the resulting ammonium chloride is filtered off and the filtrate is concentrated to obtain a crude product. The other is the use of aqueous ammonia as a reactant, where the reaction solution is extracted with a suitable organic solvent and the solvent is distilled off to obtain a crude product.

The crude product can be purified by column chromatography.

The material compounds having the general formula [II] given earlier are all new compounds and can be prepared in accordance with the following equation:

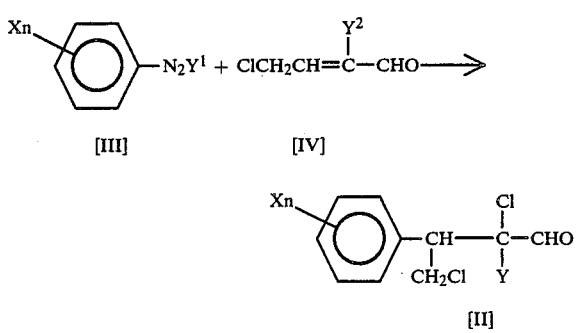

wherein

X, Y and n are as previously defined;

$Y^1$ is halogen or tetra fluoro boron; and $Y^2$ is hydrogen or halogen.

The diazonium salt having the general formula [III] can be easily obtained from the corresponding aniline.

The above reaction can be conducted in water or aqueous organic solvent in the presence of a catalyst. As aqueous organic solvent, acetone, acetonitrile, acetic acid or the like may be used. As the catalyst, cupric chloride, cupric bromide, cupric fluoride or the like may be used.

The reaction temperature may be from 10° to 30° C. and the reaction may be carried out from 10 to 24 hours.

In this reaction, crotonaldehydes having the general formula [IV] can be excessively added to improve the yield likewise Meerwein reaction. Desirably, this addition is made in an amount of 1 mole to 10 moles relative to 1 mole of diazonium salt.

After the reaction has been completed, the reaction solution is extracted with a suitable organic solvent, and the solvent was distilled off and then the residual oily material is distilled under reduced pressure to obtain the compound having the general formula [II] in good yield.

Or, without distillation for isolation, after untreated crotonaldehydes is removed, the residue can be directly used in subsequent reaction.

Furthermore, the compound having the general formula [II] can be also isolated in the way of separating the compound as a sodium hydrogen sulfite adduct from the reaction mixture and ridding the adduct of a sodium hydrogen sulfite.

The following examples illustrate the invention:

1. PRODUCTION OF A COMPOUND HAVING THE GENERAL FORMULA [I]

EXAMPLE 1-1

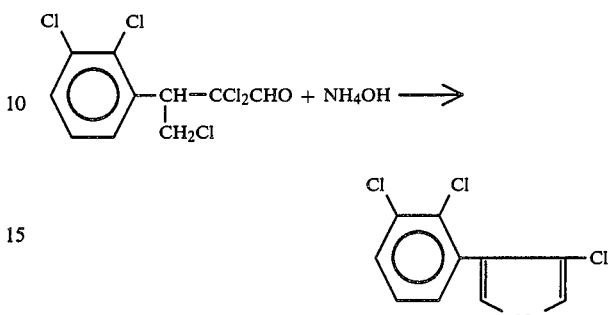

1.6 g of 2,2,4-trichloro-3-(2,3-dichlorophenyl) butylaldenhyde was dissolved in 5 ml of diglyme. After 5 ml of 28% ammonia water was added to it, the solution was heated at about 100° C. for three hours with stirring. When this was ended, 2 ml of 28% ammonia water was introduced and the mixed solution was further heated up for one hour with stirring, and then the solution was allowed to stand overnight at room temperature. The mixture was extracted with 20 ml of ethylether, and it was dried over magnesium sulfate, and the ethylether distilled off to obtain brown oily matter. The oily matter was then purified by silica gel column chromatography and as a result 0.54 g of desired product was obatined.

Melting point: 59°-60° C., Yield: 43.8%.

EXAMPLE 1-2

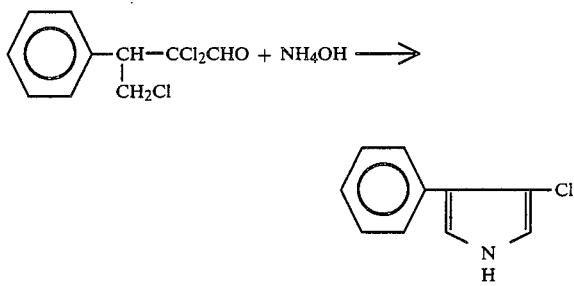

1.9 g of 2,2,4-trichloro-3-phenyl-butylaldehyde was dissolved in 10 ml of dioxane. After 5 ml of 25% ammonia water was added to it, the solution was heated at 90° C. with stirring for three hours. After 5 ml of 25% ammonia water was further added to it, the mixed solution was heated up with stirring for three hours and left to stand at room temperature for 14 hours. After the dioxane was distilled off, the solution was extracted with 20 ml of ethyl acetate, and it was washed with saturated salt-water, dried over magnesium sulfate and then the solvent was distilled off. When the crude product obtained was purified by silica gel column chromatography, 0.65 g of desired product was produced.

$n_D^{16.5}$ 1.6343, Yield: 48.5%.

EXAMPLE 1-3

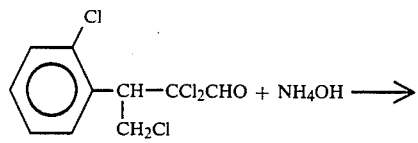

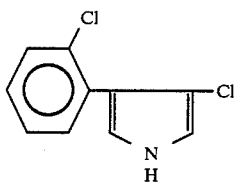

1.5 g of 2,2,4-trichloro-3-(2-chlorophenyl) butylaldehyde was dissolved in 10 ml of dioxane. 5 ml of 25% ammonia water was added dropwise to this solution and the solution was heated at 90° C. with stirring for three hours. The solution was fed with 5 ml of 25% ammonia water and was further heated up with stirring for three hours and then it was allowed to stand at room temperature for 15 hours. As soon as the dioxane was distilled off, the solution was extracted with 20 ml of ethyl acetate and it was next washed with saturated salt-water, dried over magnesium sulfate, and the solvent finally distilled off. The resultant crude product was purified with silica gel column chromatography to obtain 0.75 g of desired product.

Melting point: 68°-70° C., Yield: 67.5%.

EXAMPLE 1-4

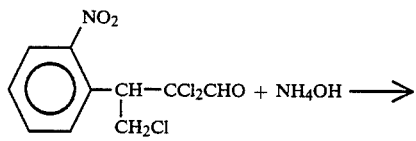

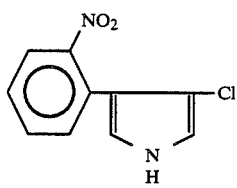

1.5 g of 2,2,4-trichloro-3-(2-nitrophenyl) butylaldehyde was dissolved in 10 ml of dioxane, and in a manner similar to that of Example 1-3, 0.8 g of desired product was obtained.

mp 111°-113° C., Yield: 64%.

EXAMPLE 1-5

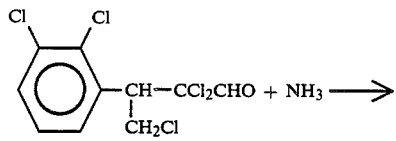

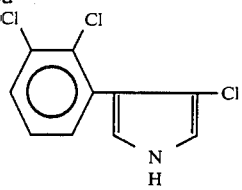

A solution of 3.2 g of 2,2,4-trichloro-3-(2,3-dichlorophenyl) butylaldehyde in 40 ml of glyme was heated and refluxed while it was ammonia gas-injected for five hours. The reaction solution was cooled down to room temperature and the precipitates that resulted were filtered out and the filtrate was fed with 0.8 g of 1,8-diazabicyclo [5,4,0]-7-undecene (D.B.U) before it was stirred overnight at room temperature. Insoluble matters were filtered out; the filtrate was concentrated under reduced pressure, and the residuals that occurred were purified by silica gel column chromatography. The result was 2 g of the desired product.

Melting point: 59°-60° C., Yield: 81%.

EXAMPLE 1-6

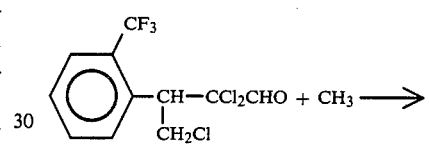

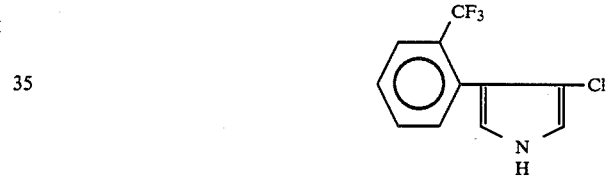

A solution of 3.1 g of 2,2,4-trichloro-3-(2-trifuluoromethyl) butylaldehyde in 40 ml of glyme was injected with ammonia gas at room temperature for three hours. Again, at 40° C., the solution was ammonia gas-injected for another three hours. After it was cooled down to room temperature, the solution was processed in a manner similar to that in Example 1-5. This produced 1.5 g of the desired product.

Melting point: 43°-52° C., Yield: 63%.

EXAMPLE 1-7

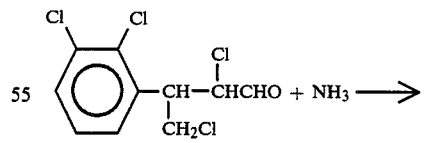

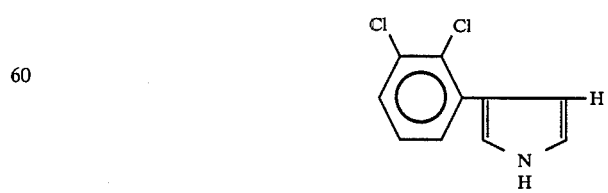

A solution of 1.5 g of 2,4-dichloro-3-(2,3-dichlorophenyl) butylaldehyde in 20 ml of glyme was injected with ammonia gas for 1 hour at 70° C. The reaction solution was cooled down to room temperature and fed with 2.4 g of D.B.U before it was stirred overnight at room temperature. The solution was concentrated under reduced pressure and the residue was extracted with ethyl acetate. The extracted solution was washed with water and dried over magnesium sulfate and then the solvent was distilled off under redused pressure. The result was 0.45 g of the desired product.

Refractive index: $N_D^{29}$ 1,6253.

2. PRODUCTION OF A COMPOUND HAVING THE GENRAL FORMULA [II]

EXAMPLE 2-1

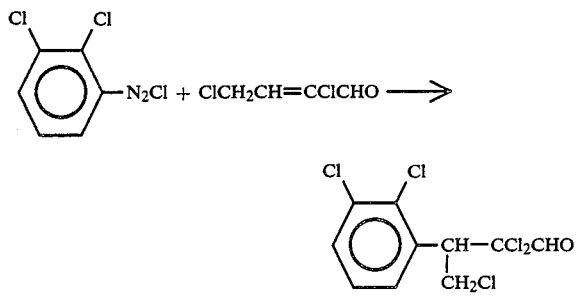

A solution of 3.8 g of sodium nitrite in 8 ml of water was added dropwise to a solution containing 8.2 g (0.05 mol) of 2,3-dichloroaniline, 10 ml of water and 15 ml of concentrated hydrochloric acid. After 20 minutes of stirring, the mixed solution was filtered to obtain a water solution of diazonium salt.

This water solution of diazonium salt was added at 0°-5° C. to a mixed solution of 4.7 g of 2,4-dichlorocrotonaldehyde (0.033 mol), 20 ml of acetone, and 9.2 g of potassium chloride. The mixture was then adjusted to pH 2 with a water solution of saturated sodium acetate, after which 1 g of cupric chloride was added to allow this to react with the mixed solution at 15°-20° C. for 18 hours. When the reaction was ended, the solution was extracted three times with 30 ml of ether, and the solution was washed with saturated salt-water and dried over magnesium sulfate. When the ether was distilled off, the oily matter obtained was distilled to obtain 4.8 g of the intended product.

Yield: 45%, Melting point: 76° C., Boiling point 140°-148° C./0.3 mmHg.

EXAMPLE 2-2

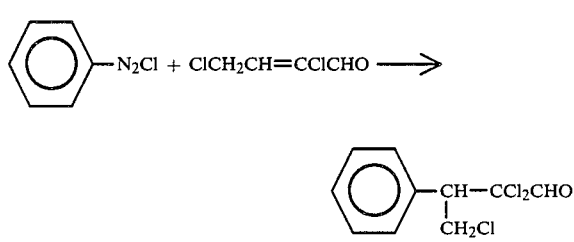

A solution of 1.3 g of sodium nitrite in 4 ml of water was added dropwise to a solution containing 1.7 g (0.018 mol) of aniline, 8 ml of water and 6 ml of concentrated hydrochloric acid. In the manner similar to Example 2-1, a water solution of diazonium salt was then prepared.

This water solution of diazonium salt was added at 0°-5° C. to a mixed solution containing 7.5 g of 2,4-dichlorocrotonaldehyde (0.053 mol), 18 ml of acetone and 1.9 g of sodium acetate.

To this was added 1.2 g of lithium chloride and 0.35 g of cupric chloride to allow them to react with each other for 18 hours at 15°-20° C. The acetone was distilled off from the reaction solution, which was then extracted two times with 40 ml of ether. The extracted solution was dried over magnesium sulfate and the ether was distilled off. The residual oily matter was distilled and the desired substance was obtained in an amount of 1.9 g.

Yield: 41.4%, Boiling point: 96°-97° C./0.15 mmHg.

EXAMPLE 2-3

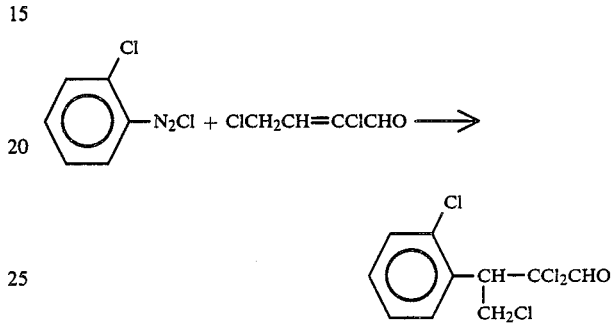

A solution of 1.2 g of sodium nitrite in 4 ml of water was added dropwise to a solution containing 2 g (0.0156 mol) of 2-chloraniline, 9 ml of water and 6 ml of concentrated hydrochloric acid. Then in a manner similar to Example 2-1, a water solution of diazonium salt was prepared.

This water solution of diazonium salt was added at 0°-5° C. to a mixed solution of 6.5 g of 2,4-dichlorocrotonaldehyde (0.0467 mol), 18 ml of acetone and 1.7 g of sodium acetate. To this was added 0.9 g of lithium chloride and 0.2 g of cupric chloride to allow them to react with one another at 15°-20° C. for 22 hours. Subsequently, in the same procedures as specified in Example 2-2, the desired product was obtained in an amount of 2.2 g.

Boiling point: 110°-115° C./0.1 mmHg, Yield: 49.0%.

EXAMPLE 2-4

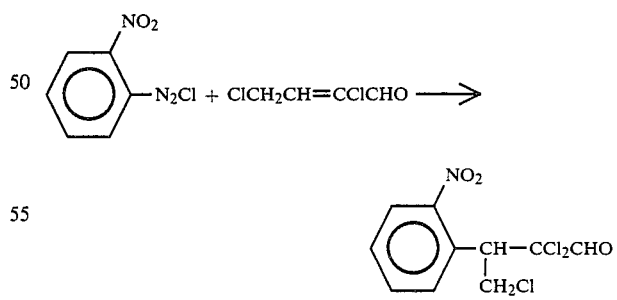

A solution of 1.2 g of sodium nitrite in 4 ml of water was added drop by drop to a solution of 2.3 g (0.016 mol) of 2-nitroaniline, 9 ml of water and 6 ml of concentrated hydrochloric acid. Then in a manner similar fo Example 2-1, a water solution of diazonium salt was prepared.

This water solution of diazonium salt was added at 0°-5° C. to a mixed solution of 6.7 g (0.0482 mol) of 2,4-dichlorocrotonaldehyde, 18 ml of acetone and 1.7 g of sodium acetate. To this was added 1 g of lithium chloride and 0.3 g of cupric chloride to make them react with one another at 15°–20° C. for 23 hours.

Thereupon 1.4 g of the desired product was obtained in the same manner as Example 2.

Boiling point: 115°–168° C./2 mmHg, Yield: 31%.

EXAMPLE 2-5

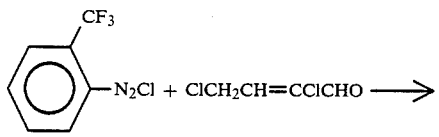

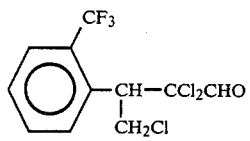

A solution of 1.2 g of sodium nitrite in 4 ml of water was added dropwise to a solution of 2.6 g of 2-aminobenzotrifluoride (0.016 mol), 9 ml of water and 6 ml of concentrated hydrochloric acid. Then the procedures in Example 2-1 were followed to prepare a water solution of diazonium salt.

At 0°–5° C., this water solution of diazonium salt was added to a mixed solution containing 6.7 g (0.0482 mol) of 2,4-dichlorocrotonaldehyde, 18 ml of acetone and 2 g of sodium acetate. To this, 1 g of lithium chloride and 0.3 g of cupric chloride were added to allow them to react with one another at 15°–20° C. for 18 hours.

Then in the same procedures as in Example 2-2, 2.3 g of desired product was acquired.

Yield: 45.1%, Boiling point: 93°–97° C./0.3 mmHg.

EXAMPLE 2-6

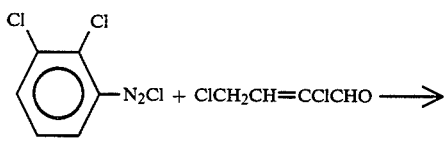

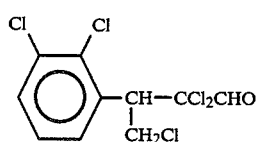

A solution of 1.9 g of sodium nitrite in 4 ml of water was added dropwise at 0°–2° C. to a solution of 4.1 g (0.025 mol) of 2,3-dichloroaniline, 5 ml of water and 7.5 ml of concentrated hydrochloric acid. At the temperature at which it was obtained, the mixed solution was stirred for 20 minutes and were filtered to produce a water solution of diazonium salt. This water solution of diazonium salt was added at 0°–5° C. to a mixed solution containing 34.75 g (0.25 mol) of 2,4-dichlorocrotonaldehyde, 5 ml of acetone and 1.86 g (0.025 mol) of potassium chloride. This mixed solution was then adjusted to pH 4.1 with a water solution of saturated sodium acetate and 0.5 g (0.0037 mol) of cupric chloride was added to allow this to react with the solution for 5 hours at 15°–20° C. After the reaction, the mixed solution was extracted three times with 30 ml of ether, and the ether-extracted solution was then washed two times with 30 ml of saturated salt-water. The solution was dried over magnesium sulfate and the ether was distilled off and the oily matter obtained was distilled to acquire 4.65 g of 2,2,4-trichloro-3-(2,3-dichlorophenyl) butylaldhyde (b.p. 140°–148° C./0.3 mmHg, mp 76° C.).

Yield: 58%.

EXAMPLE 2-7

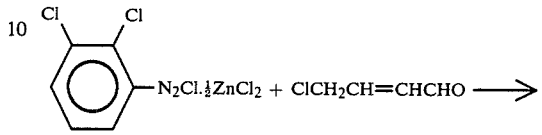

8 g of bis-(2,3-dichlorophenyl)diazonium zinc tetrachloride, 4.8 g of 4-chlorocrotonaldehyde and 1 g of potassium chloride were added in a mixed solution containing 10 ml of acetonitrile and 4 ml of water. To the solution 0.5 g of cupric chloride was added at 15° C. and it was headed slowly to allow to react with each other for 3 hours at 20° C., at which N₂ gas began to generate. The acetonitrile was distilled off from the reaction solution and the residue was extracted three times with 10 ml of ethyl ether. The extracted solution was washed three times with 10 ml of saturated salt-water and dried over magnesium sulfate. When the ether was distilled off, the residue was distilled off and 4 g of the desired material was obtained.

Boiling point 165°–173° C./5 mmHg.

EXAMPLE 2-8

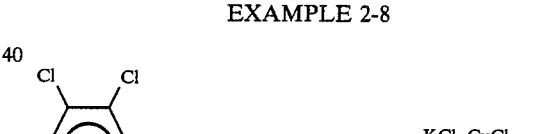

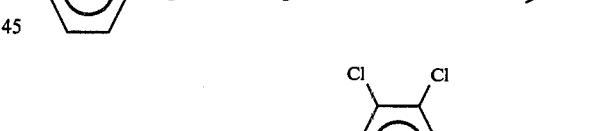

3.9 g of 2,3-dichlorophenyl diazonium tetrafluoroborate, 6.3 g of 2,4-dichlorocrotonaldehyde and 2.2 g potassium chloride were added in a mixed solution containing 10 ml of water. To the suspension 0.3 g of cupric chloride was added to react with one another at 20°–30° C. for five hours. To the reaction mixture, ethyl ether was added and it was washed with water and dried over magnesium sulfate. When ethyl ether and the excessive 2,4-dichlorocrotonaldehyde was distilled off, the residue was purified by column chromatography and 2.1 g of the sesired material was obtained.

Melting point: 76° C., Yield: 44%.

In addition to the above-mentioned compounds, some typical compounds having the general formula [II] are listed in Table 1.

TABLE 1

| Compound No. | Structural Formula | Physical Constant (boiling point) °C. |
|---|---|---|
| 1 | C₆H₅–CH(CH₂Cl)–CCl₂CHO | 96~97° C./0.15 mm Hg |
| 2 | 2-Cl-C₆H₄–CH(CH₂Cl)–CCl₂CHO | 110~115° C./0.1 mm Hg |
| 3 | 2,3-Cl₂-C₆H₃–CH(CH₂Cl)–CCl₂CHO | mp 75~76° C. |
| 4 | 2-NO₂-C₆H₄–CH(CH₂Cl)–CCl₂CHO | 155~163° C./2 mm Hg |
| 5 | 2-CF₃-C₆H₄–CH(CH₂Cl)–CCl₂CHO | 93~97° C./0.3 mm Hg |
| 6 | 2,3-Cl₂-C₆H₃–CH(CH₂Cl)–CH(Cl)CHO | 165~173° C./5 mm Hg |

What we claim is:
1. A compound having the general formula

$$X_n\text{–}C_6H_{5-n}\text{–}CH(CH_2Cl)\text{–}C(Cl)(Y)\text{–}CHO \quad [II]$$

wherein
X is halogen, nitro or haloalkyl having 1 to 3 carbon atoms;
n is 0, 1 or 2; and
Y is hydrogen or halogen.

* * * * *